United States Patent [19] [11] 4,110,540
Freitag et al. [45] Aug. 29, 1978

[54] PROCESS FOR THE PREPARATION OF MULTINUCLEAR PHENOLS WHICH ARE ALKYLATED IN THE NUCLEUS

[75] Inventors: Dieter Freitag; Erhard Tresper; Rolf Kuchenmeister; Wolfgang Beer, all of Krefeld, Germany

[73] Assignee: Bayer Aktiengesellschaft, Germany

[21] Appl. No.: 708,942

[22] Filed: Jul. 27, 1976

[30] Foreign Application Priority Data

Aug. 2, 1975 [DE] Fed. Rep. of Germany ....... 2534559

[51] Int. Cl.$^2$ ..................... C07C 37/00; C07C 37/14; C07C 39/12; C07C 39/16
[52] U.S. Cl. ..................... 568/718; 568/720; 528/153; 528/155; 528/166
[58] Field of Search ..................... 260/619 A

[56] References Cited

U.S. PATENT DOCUMENTS 3,075,832 1/1963 Ecke et al. ..................... 260/619 A
3,116,336 12/1963 Van Winkle ..................... 260/619 A

FOREIGN PATENT DOCUMENTS 905,994 9/1962 United Kingdom ..................... 260/624

Primary Examiner—Norman Morgenstern
Attorney, Agent, or Firm—Connolly and Hutz

[57] ABSTRACT

A process for the preparation of multinuclear phenols alkylated in the nucleus, wherein bisphenol A is reacted with a phenyl alkenyl compound in the presence of a catalytic quantity of aluminium phenolate and resols obtained from said alkylated phenols.

12 Claims, No Drawings

PROCESS FOR THE PREPARATION OF MULTINUCLEAR PHENOLS WHICH ARE ALKYLATED IN THE NUCLEUS

This invention relates to multinuclear phenols which are alkylated in the nucleus, to their preparation and to their use in the production of resols.

It is known to alkylate phenol with phenylalkenyl compounds, in particular with styrene or α-methylstyrene, in the presence of catalysts. An acid catalyst is generally used for this purpose, for example sulphuric acid, p-toluene sulphonic acid or phosphoric acid. The reaction products obtained are mixtures consisting of a major proportion of p-substituted phenols and varying proportions of o-substituted phenols, depending on the reaction conditions (Beilstein, E III 5, 1162).

The reaction however, may also be carried out using basic catalysts, in particular aluminium phenolate. When using aluminium phenolate as catalyst, for example, o-cumylphenol can be obtained as major reaction product together with a small amount of p-cumylphenol from the reaction of phenol with α-methylstyrene (Angew. Chemie 69, 124 (1957), Zh. Org. Khim. 10, 1974,2, 359-64).

It is by no means obvious that these conditions for alkylating monophenols should be applicable to bisphenols since, according to the known state of the art, one would expect that a reaction catalysed with acids or bases causes decomposition of bisphenol A as described in German Auslegeschrift No. 1,235,894. It is, in fact, found that the acid catalysed alkylation of bisphenol A with α-methylstyrene does not result in the desired di-, tri- and tetraalkylated bisphenol A derivatives but causes decomposition of bisphenol A and recombination to predominantly isomeric mixtures of bisphenol A as is shown in the comparison example.

It has now surprisingly been found that bisphenol A can be alkylated with phenylalkenyl compounds without undergoing significant decomposition when the reaction is carried out in the presence of aluminium phenolate as catalyst.

In contradiction to the teaching given in German Auslegeschrift No. 1,235,894, according to which bisphenols such as bisphenol A are readily and quantitatively decomposed even in presence of catalytic quantities of bases and therefore a controlled alkylation of bisphenol A is impossible, the process according to the invention succeeds in producing multinuclear phenols which are alkylated in the nucleus.

The process according to the invention has, moreover, the advantage that the side reactions of the phenylalkenyl compounds with themselves (dimerisation, trimerisation, Friedel-Crafts reactions) which occur in the presence of acid catalysts are now no longer observed.

Another advantage of the inventive process is the ease with which the aluminium phenolate used as catalyst can subsequently be removed. It need not, like the abovementioned acid catalysts, be separated by an elaborate process of neutralisation followed by washing, but can be removed simply by filtration and thus may be used again.

The present invention thus relates to a process for the preparation of multinuclear phenols alkylated in the nucleus as represented by the following general formula I

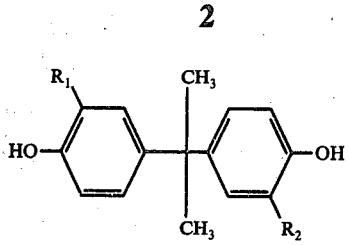

in which $R_1$ and $R_2$ are different from each other and represent a hydrogen atom or a group of formula II or $R_1$ and $R_2$ are equal and both represent a group of formula II:

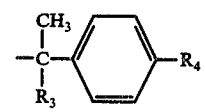

in which
$R_3$ represents a hydrogen atom or a methyl group and
$R_4$ represents a hydrogen atom or an alkyl group having from 1 to 3 carbon atoms or a group of formula III

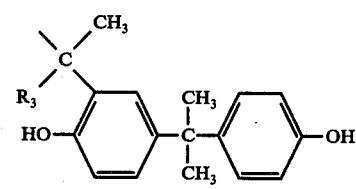

in which $R_3$ has the meaning given above, or mixtures of the multinuclear phenols represented by the general formula I which may contain from 0 to 80% by weight of bisphenol A, wherein bisphenol A is reacted with a phenylalkenyl compound of the formula IV

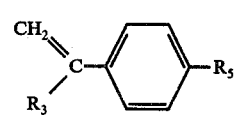

in which
$R_3$ has the meaning specified above and
$R_5$ represents hydrogen or an alkyl group having from 1 to 3 carbon atoms or a group of formula V

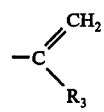

in which $R_3$ has the meaning specified above, in the presence of catalytic quantities of aluminium phenolate and, optionally, in the presence of a solvent and/or diluent and/or dispersing agent and at temperatures of from 70° to 180° C, preferably between 90° and 140° C.

Bisphenol A [bis(4-hydroxy phenyl)-isopropane] is used as a starting compound.

The other starting compounds used are phenylalkenyl compounds of formula IV. Compounds, for example styrene or α-methylstyrene and bisphenol A are manufactured on a large commercial scale and therefore are easily obtainable. The alkyl or alkenyl compounds such as p-methyl styrene, divinylbenzene or diisopropenylbenzene are also available commercially or obtainable by known simple processes. Suitable precursors of these compounds may, of course, also be used, for example dimethylphenylcarbinol or α,α'-bis-hydroxy-α,αα',α'-tetramethyl-p-xylene. When using these compounds, it has been found advantageous to remove the water of reaction by azeotropic distillation during the reaction.

The molar ratios of bisphenol A to phenylalkenyl compounds may vary within a wide range. In the presence of a solvent, diluent or dispersing agent the starting compounds are advantageously reacted together in stoichiometric quantities or in the absence of a solvent the phenylalkenyl compound is used in excess.

The molar ratios of bisphenol A to phenylalkenyl compounds employed are generally from 0.2 to 30 and, preferably from 0.5 to 15.

The inventive process, is carried out in the presence of aluminium phenolate as catalyst.

The quantity of catalyst used may vary over a wide range but only catalytic quantities are required for carrying out the process of the invention. It has been found that good yields are obtained when using the catalyst in quantities of from 0.2 to 25% by weight, preferably from 1 to 10% by weight, based on bisphenol A.

The reaction time is very variable and may vary from a few minutes to many hours, depending on whether the reaction is carried out batchwise in a reaction vessel or pressure vessel or continuously, for example in the liquid or gaseous phase over a solid bed or fluidised bed catalyst in a reaction tube. Another factor which influences the reaction time is the degree of conversion. For achieving controlled production of monoalkylation products, it may be advisable not to react the bisphenol A completely whereas, for producing dialkylation products, it may be advantageous to employ longer reaction times and to continue to a more complete conversion of the starting materials. Similar considerations apply to the production of mixtures containing given ratios of the individual components. The necessary reaction conditions for achieving the desired results can easily be determined by simple preliminary tests.

Suitable technical procedures and apparatus for carrying out the process according to the invention are known in the art and already available.

The process according to the invention may be carried out at temperatures of between 70° and 180° C, preferably between 90° and 140° C.

The process according to the invention is generally carried out at normal pressure although excess or reduced pressure may be employed. An inert gas such as nitrogen, helium or argon may be used and is recommended for obtaining colourless reaction mixtures.

Optionally the process according to the invention can be carried out in the presence of a suitable solvent and/or diluent and/or dispersing agent. Compounds which are inert under the reaction conditions may be used for this purpose, for example hydrocarbons with $C_6$ to $C_{10}$ such as benzene, toluene, xylene, durene, tetraline, naphthalene, paraffin oil or halogenated hydrocarbons with $C_1$ to $C_{18}$ in particular chlorinated aromatic hydrocarbons such as chlorobenzene, dichlorobenzene, chloronaphthalenes or chloroalkanes such as 1,2-dichloroethane or carbon tetrachloride; also ethers with $C_4$ to $C_{12}$ such as diphenylether, esters with $C_4$ to $C_{12}$ such as benzene dicarboxylic acid dimethyl ester or nitrobenzene.

According to one particularly advantageous method of carrying out the inventive process styrene or α-methylstyrene functions as the phenylalkenyl component and as solvent and/or diluent. This method of carrying out the process is particularly to be recommended, for the preparation of dialkylation products or mixtures containing a high proportion of dialkylation products.

Since the reaction products are obtained in a high degree of purity the reaction mixture is very easily processed. For example, the catalyst can be separated from the hot reaction mixture by filtration and then used again. When the reaction is carried on only to a low degree of conversion of bisphenol A, for example in order to produce a monoalkylation product, bisphenol A crystallises as a 99% pure product as the reaction solution cools down, and can be used again. The remaining solution generally contains only small quantities of dialkylation product in addition to a little phenol and bisphenol A. The monoalkylation product can easily be isolated from this solution by distillation in a high vacuum. Isolation by fractional crystallisation is also no problem.

If the main reaction products are dialkylation products isolation from the reaction mixture separated from bisphenol A is achieved by fractional crystallisation.

If the reaction mixtures contain preferably 5 to 75% by weight of compounds of formula I wherein $R_1$ represents hydrogen and $R_2$ does not represent hydrogen; 2 to 65% by weight of compounds of formula I wherein $R_1$ and $R_2$ do not represent hydrogen and 0 to 80% by weight of bisphenol A, the reaction products can be separated quite simple since it merely requires filtration and concentration by evaporation. If the reaction mixture obtained is not immediately concentrated by evaporation but the reaction solution is left to cool after filtration, bisphenol A crystallises and can be removed. This provides a simple method, apart from controlling the reaction conditions, of obtaining a given proportion of bisphenol A in the mixtures.

The process can be explained by the reaction scheme representing the preparation of 4-(4'-hydroxy-α,α-dimethylbenzyl)-2-α,α-dimethylbenzylphenol:

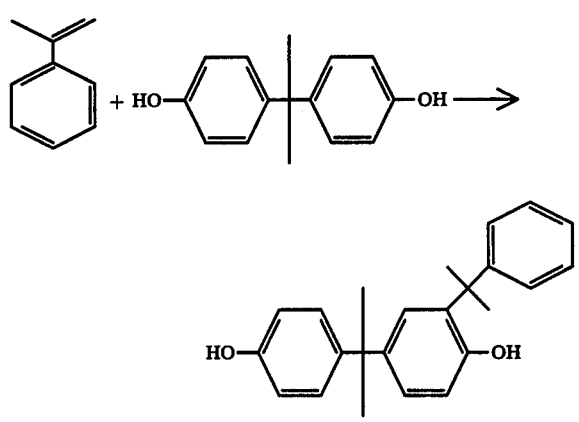

Compounds of formula I prepared by the process according to the invention or mixtures thereof, which may contain bisphenol A, are particularly suitable for the production of polymers and lacquer raw materials, for example by reaction with epichlorohydrin, cyanogen chloride or dicarboxylic acids or their derivatives such as phosgene, maleic acid anhydride or phthalic acid anhydride, or by reaction with formaldehyde for the production of novolaks.

Mixtures of multinuclear phenols alkylated in the nucleus prepared by the process according to the invention are particularly suitable for the production of resol resins which have excellent properties. The resol resins obtained by alkaline addition of formalin to the mixtures of nuclear alkylated bisphenols according to the invention are completely colourless when cured to resites. When they have been cured in combination with epoxide resins, the resites have such a high degree of elasticity that metal surfaces coated with such products can be processed to produce shaped products without damage to the lacquer film. In addition, these lacquer films have a surprisingly high resistance to steam at 121° C (sterilisation test). By stoving these new resol resins and the corresponding combinations of resol resins with epoxide resins give colourless lacquers capable of being deep drawn and sterilised. They are another object of this invention.

Particularly suitable for the production of the resol resins according to the invention are mixtures consisting of from 3 to 75% by weight of bisphenol A, 20 to 75% by weight of a monoalkylated bisphenol A derivative of the general formula I ($R_1$ does not represent H but a group of the formula II, $R_2$ represents H), 2 to 45% by weight of a dialkylated bisphenol A derivative of the general formula I ($R_1$ and $R_2$ represent a group of the formula II) and 0 to 4% by weight of phenol and/or unknown components which may be formed during the aluminium phenolate catalysed alkylation of bisphenol A with phenylalkenyl compounds in addition to the products mentioned above.

Production of the resols according to the invention is carried out by heating the hydroxyl containing mixture in an alcohol such as methanol, ethanol, propanol, butanol, isopropanol or isobutanol with 25 to 35% aqueous formaldehyde or a formaldehyde donor such as paraformaldehyde, and a basic catalyst.

The reaction temperature employed is from 30° to 140° C, preferably from 50° to 117° C.

The reaction time required depends on the reaction temperature and the quantity of catalyst. It lasts generally from 1 to 12 hours. The ratio by weight of formaldehyde (100%) put into the process to hydroxyl containing starting mixture ranges from 1:10 to 2:5. Suitable catalysts include basic compounds such as lithium hydroxide, potassium hydroxide, sodium hydroxide, calcium hydroxide, ammonia, sodium hydroxide, sodium and potassium carbonate, barium hydroxide and mixtures of any of these catalysts. Water-soluble amines such as dimethylethanolamine may also be used as catalysts. The quantity of catalyst used can be varied from 0.01 to 1 mol for every 300 g of condensation resin put into the process.

The process of the reaction mixture is very simple. The mixture is neutralised with a dilute acid such as sulphuric acid, hydrochloric acid, phosphoric acid, benzoic acid, acetic acid, carbonic acid or lactic acid and concentrated by evaporation or, alternatively, the organic phase is separated after the addition of water and concentrated to the desired visocisty by evaporation in a vacuum.

Curing the resol to covert it into the resite is carried out using a solution of the resol with or without the addition of an epoxide resin (such as Epikote 1007 ® manufactured by Shell) in a typical lacquer solvent such as methanol, butanol, isobutanol, benzene/butanol, ethyl acetate, xylene, ethyl glycol acetate or methyl ethyl ketone applied as a thin film to a metal surface. The usual levelling agents may be added to the solution. An insoluble lacquer having the properties indicated above is obtained by heating to temperatures of from 100° to 300° C, preferably 120° to 200° C. Curing may also be carried out in the presence of catalytic quantities of acids such as hydrochloric acid, phosphoric acid, oxalic acid, p-toluenesulphonic acid, boric acid or lactic acid. Curing may also be carried out on a mixture with melamine resins, polyester resins or polycarbonates, with or without acid.

The resols according to the invention are also suitable for the manufacture of blocks, boards, rods, tubes and sections (used as casting resins) and for the manufacture of foams and, by application of heat and pressure with or without fillers, they may also be used for the production of pressure moulded articles.

The resols according to the invention may also be advantageously used for the same purposes as resol resins produced from phenol. The resites according to the invention are also particularly suitable for electric insulating purposes.

All percentages in the examples are percentages by weight.

EXAMPLE 1

456 g of Bisphenol A (2 mol) together with 45 g of aluminium phenolate and 236 g of α-methylstyrene (2 mol) are dissolved or suspended in 1800 cc of toluene under an atmosphere of nitrogen. The mixture is heated to reflux, the contents of the flask reaching a temperature of 116° C. After 6 hours, the hot reaction solution is freed from aluminium phenolate by filtration. By cooling the solution slowly to room temperature, 143 g of unreacted bisphenol A crystallise (purity 99%, determined gas chromatographically after silylation). The mother licquor is concentrated by evaporation and a high vacuum is finally applied. 36 g of compounds distilling within the boiling range of phenol can be isolated. The residue weights 478 g and contains 0.3% of phenol, 12% of bisphenol A, 73% of the monoalkylation product 4-(4'-hydroxy-α,α-dimethylbenzyl)-2-α,α-dimethylbenzylphenol and 12% of the dialkylation product 4-[4'-hydroxy-(3'-α,α-dimethylbenzyl)-α,α-dimethylbenzyl]-2-α,α-dimethylbenzylphenol. In addition, the mixture contains less than 1% of each of four other compounds which were not investigated.

EXAMPLE 2

A mixture of 456 g of bisphenol A (2 mol), 15 g of aluminium phenolate and 1180 g of α-methylstyrene (10 mol) is stirred for one hour at 120° to 124° C under an atmosphere of nitrogen. The aluminium phenolate is separated from the hot solution by filtration. Unreacted α-methylstyrene is distilled off in a water jet vacuum and, finally, 23 g of compounds which distil off within the boiling range of phenol are removed under a high vacuum. 738 g of residue are obtained, consisting of 10% of bisphenol A, 42% of the monoalkylation product described in Example 1 and 45% of the dialkylation product described in Example 1 (gas chromatographically after silyation) in addition to five other, uninvestigated compounds together amounting to 3%.

EXAMPLES 3 TO 8

In the reactions represented in the following Table, the reactants together with aluminium phenolate and solvent were heated to the given reaction temperature under stirring. After the given reaction time, the aluminium phenolate was separated from the hot solution by filtration. The filtrate was freed from solvent by distillation and then partly distilled at a temperature of 130° C and a vacuum of 1 mm. The resulting residue was investigated gas chromatographically after silylation and the proportions of the following three components were determined in percent by weight:

Component I: unreacted bisphenol A
II: 4-(4'-Hydroxy-α,α-dimethylbenzyl)-2-α,α-dimethylbenzyl-phenol
III: 4-[4'-Hydroxy-3'-α,α-dimethylbenzyl)-α,α-dimethylbenzyl]-2-α,α-dimethylbenzyl-phenol.

| Ex. | Bisphenol A mol | α-methyl-styrene mol | aluminium phenolate g | solvent | Reaction temperature °C | time hours | Component I | II | III |
|---|---|---|---|---|---|---|---|---|---|
| 3 | 2 | 2 | 15 | toluene 400 ml | 122–125 | 4 | 40 | 36 | 21 |
| 4 | 2 | 2 | 30 | xylene 400 ml | 120 | ½ | 56 | 37 | 4 |
| 5 | 2 | 2 | 15 | toluene 1500 ml | 120 | 3 | 67 | 29 | 2 |
| 6 | 2 | 2 | 45 | toluene 1800 ml | 117 | 10 | 10 | 46 | 36 |
| 7 | 2 | 11.3 | 45 | — | 160 | ½ | 3 | 55 | 39 |
| 8 | 2 | 2 | 15 | toluene 1800 ml | 116 | 12 | 30 | 49 | 17 |

EXAMPLE 9

(Comparison Example)

228 g of bisphenol A and 5 g of 25% sulphuric acid are heated to 140° C ±5° C and 472 g of α-methylstyrene are slowly added at this temperature. The reaction mixture is then cooled to 75°–80° C, neutralised with 30 ml of aqueous sodium bicarbonate solution and taken up in 1000 ml of toluene. After phase separation and drying, toluene and α-methylstyrene are distilled off in a water jet vacuum and the resulting residue is partly distilled at a reaction temperature of 130° C and a vacuum of 0.1 mm. 280 g of decomposition products can be distilled off within a boiling range of 50° to 126° C/0.1 mm. The residue of this distillation was investigated gas chromatographically after silylation. Numerous compounds are found, including 53% of bisphenol A, 11% of o,p-bisphenol A, 12% of other compounds boiling within the same range, 1.2% of 4-(4'-hydroxy-α,α-dimethylbenzyl)-2-α,α-dimethylbenzyl-phenol, 9.4% of compounds boiling within the same range and 3% of 4-[(4'-hydroxy-3-α,α-dimethylbenzyl)-α,α-dimethylbenzyl]-2-α,α-dimethylbenzyl-phenol.

EXAMPLE 10

456 g of bisphenol A, 400 ml of toluene and 15 g of aluminium phenolate are heated to 120° C ±3° C with stirring and 208 g of styrene are added dropwise over a period of 10 minutes. 1200 ml of toluene are added after one hour, the temperature of the reaction mixture thereby dropping to 115° C. The reaction mixture is filtered hot and the filtrate is freed from solvent by distillation and partly distilled at a reaction temperature of 130° C and a vacuum of 1 mm. The resulting residue is investigated gas chromatographically after silylation. It is found to contain 49% of unreacted bisphenol A, 39% of 4-(4'-hydroxy-α,α-dimethylbenzyl)-2-α-methylbenzyl-phenol and 9% of 4-[(4'-hydroxy-3'-α-methylbenzyl)-α,α-dimethylbenzyl]-2-α-methylbenzyl phenol, the remaining 3% being made up of four other compounds.

EXAMPLE 11

4-(4'-Hydroxy-α,α-dimethylbenzyl)-2-α,α-dimethylbenzyl-phenol

Bisphenol A slightly contaminated with the monoalkylation product can be removed from the residue obtained in Example 1 by dissolving the residue in a small quantity of hot toluene. When petroleum hydrocarbons are added to the remaining mother liquor, 4-(4'-hydroxy-α,α-dimethylbenzyl)-2α,α-dimethylbenzyl-phenol crystallises with a degree of purity of more than 95%. The dialkylation product remains in solution. By renewed recrystallisation from toluene/n-hexane, 302 g of the monoalkylation product is obtained more than 98% pure (Yield: > 65%, based on the degree of conversion). This product melts at 86°–88° C.

$C_{24}H_{26}O_2$ (346.5)

Calculated: C, 83.20; H, 7.56; O, 9.24; phenol.OH, 9.81%

Found: C, 82.7; H, 7.68; O, 9.42; phenol.OH, 9.80%.

NMR (CDCl$_3$, using TMS as internal standard)

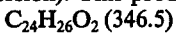

τ = 8.41 (CH$_3$), 8.35 (CH$_3$), AB system, disturbed, with τ = 3.08 as centre (Ar), = 2.72 (Ar) ppm.

Surface ratio: 6 : 6 : 7 : 5.

Another method of processing the reaction products consists of distillation under a high vacuum of the residue obtained after removal of the low boiling constituents. The colourless oil which distils over at 195° to 210° C/0.1 Torr is recrystallised from toluene/n-hexane.

EXAMPLE 12

4-[4'-Hydroxy-(3'-α,α-dimethylbenzyl)-α,α-dimethylbenzyl]-2-α,α-dimethylbenzyl-phenol The monosubstitution product and bisphenol A are removed from the residue obtained in Example 6 by crystallisation with toluene/petroleum hydrocarbons. The dialkylation product is left in the mother liquor and can be isolated by evaporation and purified by retreatment with toluene/n-hexane. A highly viscous oil which solidifies as a vitreous product without crystallisation is obtained. An analytically pure sample melts at 48° to 54° C.

$C_{33}H_{36}O_2$ (464.7)

Calculated: O, 85.30; H, 7.81; O, 6.88; phenol.OH, 7.31%

Found: O, 85.72; H, 7.94; O, 6.54; phenol.OH, 7.1%.

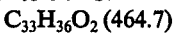

NMR (CDCl$_3$, TMS as internal standard)
$\tau = 8.39, 8.34$ (CH$_3$)
Surface ratio: 1:2.
Preparation of the resol resins:

EXAMPLE 13

277 g of a mixture of 40% by weight of bisphenol A, 36% by weight of 4-(4'-hydroxy-α,α-dimethylbenzyl)-2-α,α-dimethylbenzyl-phenol, 21% by weight of 4-(4'-hydroxy-3'-α,α-dimethylbenzyl)-α,α-dimethylbenzyl)-2-α,α-dimethylbenzylphenol prepared according to Example 3, 604 g of n-butanol, 200 g of 30% aqueous formalin solution and 4.75 g of 45% aqueous sodium hydroxide solution are heated to 90° C and kept at this temperature for 6 to 7 hours. After neutralisation with dilute phosphoric acid and washing with water, the organic phase is concentrated to the desired solids content by evaporation. 410 g of a pale yellow 76% solution of the resol resin in n-butanol are obtained.

EXAMPLES 14 TO 16

Other resol resins were obtained by the process described in Example 13.

| Ex. | Starting material | Resol resin | Solution in n-butanol % |
|---|---|---|---|
| 14 | Mixture of multinuclear phenols according to Ex. 1 | 449 g | 70 |
| 15 | " 5 | 529 g | 60 |
| 16 | " 8 | 509 g | 62 |

The resol resins obtained in this way were mixed with Shell's epoxide resin Epikote 1007 ®. An approximate 55% solution of this combination in a mixture of butanol and ethyl glycol acetate as solvents was applied to a metal sheet and stoved at 200° C for 10 minutes.

17. Comparison Example

A resol resin was prepared in a similar manner to Example 13 but using phenolalone, and the resol resin was stoved as indicated above in combination with the epoxide resin at 180° C for 12 minutes.

18. Comparison Example

A resol resin was prepared in a similar manner to Example 13 but using bisphenol A alone and the resol resin was stoved as indicated above in combination with the epoxide resin at 180° C for 12 minutes.

The properties of the lacquers are compared in the following Table:

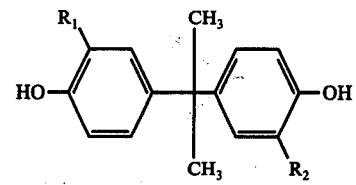

in which
R$_1$ and R$_2$ are different from each other and represent a hydrogen atom or a group of formula II or
R$_1$ and R$_2$ are equal and both represent a group of formula II

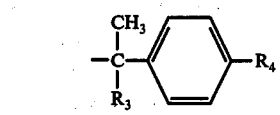

in which
R$_3$ represents a hydrogen atom or a methyl group and
R$_4$ represents a hydrogen atom, an alkyl group or a group of formula III

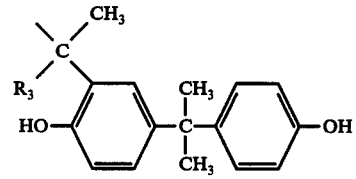

in which R$_3$ has the meaning specified above or mixtures of the multinuclear phenols represented by the general formula I which may contain from 0 to 80% by weight of bisphenol A, wherein bisphenol A is reacted with a phenyl alkenyl compound of the formula IV

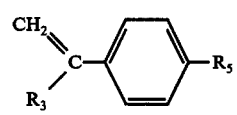

in which
R$_3$ has the meaning specified above and
R$_5$ represents hydrogen, an alkyl group or a group of formula V

|  | Resol according to Example: | | | | | |
|---|---|---|---|---|---|---|
|  | 13 | 14 | 15 | 16 | 17 | 18 |
| Ratio (based on solids content) of resol to epoxide resin | 1:2 | 1:2 | 1:2 | 1:2 | 1:2 | 1:2 |
| phosphoric acid % | 0.4 | 0.4 | 0.4 | 0.4 | 0.5 | 0.5 |
| Thickness of layer g/m$^2$ | 6.7 | 6.05 | 6.45 | 6.65 | 6 | 5.5–6 |
| Capacity for being deep drawn */ | ⅔ | 3 | 2/3 | 3 | 4 | ⅔ |
| Sterilisation */ | 2 | 2 | 3 | ⅔ | 4 (water patches) | 5 |
| Yellowing **/ | 0 | 0 | 0 | 0 | 4 | 1 |

All the products shown in the Table were cross-linked after stoving (insoluble in methyl ethyl ketone)
*/ The lower the figure, the better the lacquer can be deep drawn
**/ 0 = colourless, 4 = yellow

What we claim is:
1. A process for the preparation of a multinuclear phenol alkylated in the nucleus, of the general formula I

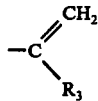 V in which R₃ has the meaning specified above, in the presence of a catalytic quantity of aluminium phenolate.

2. A process as claimed in claim 1 wherein $R_4$ represents an alkyl group which contains from 1 to 3 carbon atoms.

3. A process as claimed in claim 1 wherein $R_5$ represents an alkyl group which contains from 1 to 3 carbon atoms.

4. A process as claimed in claim 1 wherein the reaction is carried out at a temperature of from 70° to 180° C.

5. A process as claimed in claim 4 wherein the reaction is carried out at a temperature of from 90° to 140° C.

6. A process as claimed in claim 1 wherein the reaction is carried out in the presence of a solvent and/or diluent and/or dispersing agent.

7. A process as claimed in claim 1 wherein the molar ratio of bisphenol A to the phenylalkenyl compound is from 0.2:1 to 30:1.

8. A process as claimed in claim 7 wherein the molar ratio of bisphenol A to the phenylalkenyl compound is from 0.5:1 to 15:1.

9. A process as claimed in claim 1 wherein the catalyst is used in a combination of from 0.2 to 25% by weight, based on bisphenol A.

10. A process as claimed in claim 9 wherein the catalyst is used in a concentration of from 1 to 10% by weight, based on bisphenol A.

11. A process as claimed in claim 6 wherein the solvent, diluent or dispersing agent is a hydrocarbon; halogenated hydrocarbon; ether or ester.

12. A process as claimed in claim 11 wherein the solvent, diluent or dispersing agent is benzene, toluene, xylene, durene, tetraline, naphthalene, paraffin oil, chlorobenzene; dichlorobenzene; chloronaphthalene; 1,2-dichloroethane; carbon tetrachloride; diphenylether; benzene dicarboxylic acid dimethyl ester or nitrobenzene.

* * * * *